United States Patent [19]

Valdiserri et al.

[11] 4,413,077
[45] Nov. 1, 1983

[54] OLIGOMERIC AROMATIC POLYPHOSPHITES

[75] Inventors: Leo L. Valdiserri, Belpre, Ohio; Ingenuin Hechenbleikner, West Cornwall, Conn.

[73] Assignee: Borg-Warner Chemicals, Inc., Parkersburg, W. Va.

[21] Appl. No.: 275,575

[22] Filed: Jun. 22, 1981

[51] Int. Cl.$^3$ .......................... C07F 9/15; C08K 5/52
[52] U.S. Cl. ............................... 524/120; 260/927 R; 528/169
[58] Field of Search .................... 260/927 R; 524/120; 528/169

[56] References Cited

U.S. PATENT DOCUMENTS 3,053,878  9/1962  Friedman et al. .............. 260/927 R
3,305,608  2/1967  Baranauckas et al. .............. 260/921

FOREIGN PATENT DOCUMENTS 2041938  9/1980  United Kingdom ............ 260/927 R

OTHER PUBLICATIONS

Translation of Japanese Application 1975-35097, published Nov. 13, 1975.

Primary Examiner—Anton H. Sutto
Attorney, Agent, or Firm—Joseph Shekleton

[57] ABSTRACT

Aromatic, phenol-free polyphosphites containing at least two pentaerythritol residues and three bis-phenolic residues. They are effective polymer additives and are especially useful in enhancing the thermal stability of polypropylene.

10 Claims, No Drawings

OLIGOMERIC AROMATIC POLYPHOSPHITES

The invention of this application relates to aromatic polyphosphites and, in particular, to those aromatic polyphosphites which are of relatively high molecular weight. More particularly, it relates to the stabilization of olefin polymer compositions by the presence therein of small proportions of oligomeric aromatic polyphosphites.

BACKGROUND OF THE INVENTION

The aromatic polyphosphites of this invention are useful as organic polymer stabilizers. They are especially useful for such purpose in olefin polymer compositions, which require a high degree of thermal stability. One of the advantages of polypropylene, for example, is the fact that it is readily processed and fabricated in all of the conventional systems; these include solid and foam molding, solid and composite extrusion, spinning and orienting, rotocasting, powder coating, thermoforming and pressure forming, stamping and laminating. Moreover, post-fabrication operations which are commonly applied include machining, welding, turning, sawing, drilling, butt and spin welding, and hot stamping. Many of these operations are carried out at relatively high temperatures, however, and it is necessary to protect the polypropylene from thermal degradation at these temperatures.

Polypropylene is especially vulnerable to degradation under conditions which favor oxidation, for example, because of the recurring presence in the molecular chain of tertiary carbon atoms. These are notoriously susceptible to oxidative attack.

The problem of oxidative degradation generally is met by incorporation into the olefin polymer composition of a small proportion of a high molecular weight antioxidant. Phenolic phosphite antioxidants are well known and, in most instances, are quite suitable for this purpose. They frequently suffer one disadvantage, however, because of the invariable contamination of the antioxidant with a small proportion of phenol. Such contamination tends to render the polypropylene unsuitable for uses involving probable contact with food, medicines and the like. The contamination arises from the fact that the high molecular weight phenolic phosphite compounds are prepared by a transesterification reaction involving triphenyl phosphite or a phosphorus ester prepared from triphenyl phosphite, and a bisphenol. The product which results from such a reaction contains phenol as a by-product, and it is not practical to remove all of this phenol from the desired product.

U.S. Pat. No. 3,053,878 (Friedman et al.) shows the reaction of diphenyl pentaerythritol diphosphite with bisphenol A in the presence of a diphenyl phosphite catalyst to form a polymeric phosphite.

U.S. Pat. No. 3,305,608 (Baranauckas et al.) shows the reaction of stoichiometric quantities of triphenyl phosphite, pentaerythritol and 4,4-isopropylidenediphenol (bisphenol A) in the presence of a sodium catalyst.

Japanese Patent Publication No. 1975-35097 shows the reaction of triphenyl phosphite and pentaerythritol to form an intermediate product which then is reacted with a mixture of more pentaerythritol and bisphenol A. Stoichiometric quantities are used. The resulting product is said to be effective as a polymer stabilizer.

U.K. Pat. No. 2,041,938 shows a process for preparing aromatic polyphosphites which involves the reaction of dichloro pentaerythritol diphosphite with certain bis-phenolic compounds including 4,4'-butylidene-bis-(6-tertiarybutyl-m-cresol) and bis-(4-hydroxy-2-methyl-5-tertiarybutylphenyl) sulfide. The product of such process is an oligomer.

SUMMARY OF THE INVENTION

The invention of the present application is an oligomeric, phenol-free, polyphosphite conforming to the structural formula:

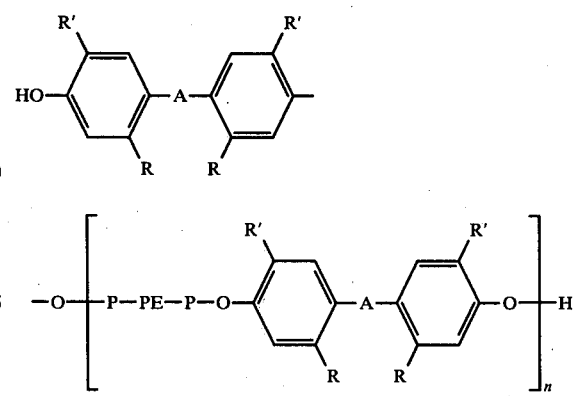

where R is methyl or hydrogen, R' is a tertiary alkyl, cycloalky or phenylalkyl group of 4–10 carbon atoms, A is alkylidene or sulfur, PE is a pentaerythritol residue and n is at least 2 and may be as large as 10.

DETAILED DESCRIPTION OF THE INVENTION

The process of preparing the aromatic polyphosphites of the present invention does not utilize triphenyl phosphite at any stage, nor any other reactant that can, upon hydrolysis, yield phenol. The resulting product thus is not contaminated with phenol and, in this respect, is entirely suitable for use in olefin polymer compositions which are intended for uses which may bring them in contact with food or medicines. The process involves preparing a phenolic antioxidant composition by reacting a pentaerythritol diphosphite compound having the structure:

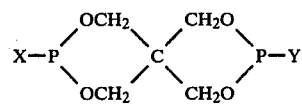

where X and Y are the same or different group selected from the class consisting of halo, amino, di-(lower alkyl) amino, morpholino and methylanilino, with a stoichiometrically excessive amount, up to about 5 mols per mol, of a bis-(hindered phenolic) compound having the structure:

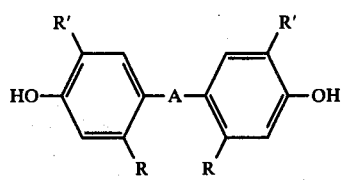

where R' is the same or different tertiary alkyl, cycloalkyl or phenylalkyl group, R is methyl or hydrogen, and A is alkylidene or sulfur.

The X and Y groups on the pentaerythritol diphosphite reactant are, in the circumstances here, known as "leaving" groups. That is, they "leave" the pentaerythritol diphosphite nucleus and are replaced in each case by the phenolic group of a bis-(hindered phenolic) compound. The reaction is illustrated below:

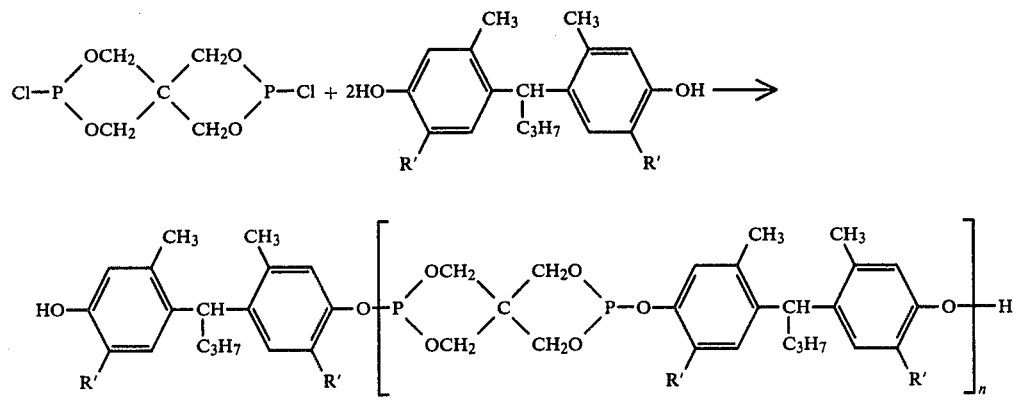

where R' is a tertiary alkyl, cycloalkyl or phenylalkyl group and n is at least 2.

As indicated, the bis-(hindered phenolic) compound is characterized by the presence of a tertiary alkyl, cycloalkyl or phenylalkyl group which is ortho to a phenolic group. This particular group may contain 4–10 carbon atoms and preferably is tertiary butyl. Other suitable groups include tertiary amyl, 1,1,2-trimethylpropyl, 1-methyl-2-ethylpropyl, 1,1-diethylpropyl, 1-methyl-1-ethylpentyl, cyclohexyl, cyclopentyl, 2-methylcyclohexyl and phenylethyl.

The alkylidene group may contain 1–10 carbon atoms. Methylene and butylidene are preferred because of the ready availability of bis-(hindered phenolic) compounds containing such alkylidene groups, but others are suitable and include isopropylidene, ethylidene, hexylidene, etc.

With respect to the pentaerythritol diphosphite compound, the X and Y groups may, as indicated, be halo, amino, di-(lower alkyl) amino, morpholino or methylanilino. Preferably, they are each chloro.

The process may be carried out in a solvent although a solvent is ordinarily unnecessary. Suitable solvents include toluene, benzene, chloroform, carbon tetrachloride, dioxane, chlorabenzene, etc. Ordinarily, it is necessary merely to mix the reactants and heat the mixture which suitable agitation.

When the leaving groups, i.e., X and Y in the pentaerythritol diphosphite, are chloro the process can be carried out as above, or a hydrogen chloride acceptor may be used. In such case, it is advisable to use a solvent also. The hydrogen chloride acceptor may be any basic amine, and lower molecular weight, aliphatic, tertiary amines are preferred. These include trimethyl amine, triethyl amine, tripropyl amine, i.e., those having up to 10 carbon atoms.

The process by which the polyphosphites of the invention may be prepared is illustrated by the following examples.

EXAMPLE 1

To a solution of 221.6 g. (0.58 mol) of 4,4'-butylidene-bis-(6-tertiarybutyl-m-cresol) and 117.2 g. (1.11 mol) of triethyl amine in 800 g. of toluene is added, over a period of one hour, a solution of 145.8 g. (0.55 mol) of dichloro pentaerythritol diphosphite in 500 g. of toluene. The resulting solution is heated at reflux temperature and filtered. The solid triethyl amine hydrochloride is removed by filtration and the filtrate is concentrated by heating to a final temperature of 165° C./5 mm. The solid residual product (81% of the theoretical yield) is shown to have an acid number of 1.7 and an average molecular weight of 1670 (corresponding to three bis-phenolic residues and two pentaerythritol residues).

EXAMPLE 2

A stirred mixture of 35.8 g. (0.094 mol) of 4,4'-butylidene-bis-(6-tertiarybutyl-m-cresol) and 8.75 g. (0.033 mol) of dichloro pentaerythritol diphosphite is heated at 170° C. (under reduced pressure) for two hours, then cooled to room temperature. The solid residue weighs 42.1 g., has an acid number of 1.35 and melts at 130°–170° C.

EXAMPLE 3

A stirred mixture of 35.8 g (0.10 mol) of bis-(4-hydroxy-2-methyl-5-tertiarybutylphenyl) sulfide and 17.5 g. (0.066 mol) of dichloro pentaerythritol diphosphite is heated under reduced pressure at 170° C. for two hours, then allowed to cool to room temperature. The residue weighs 48 g. and has an acid number of 0.37.

EXAMPLE 4

A solution of 17.0 g. (0.05 mol) of bis-(4-hydroxy-3-methyl-5-tertiarybutylphenyl) methane and 20.2 g. (0.20 mol) of triethylamine in 100 ml. of tetrahydrofuran is added dropwise over a two-hour period to a stirred solution of 13.25 g. (0.05 mol) of dichloro pentaerythritol diphosphite in 100 ml. of tetrahydrofuran. Stirring at room temperature is continued for an additional 20 hours whereupon the product mixture is filtered yielding solid triethylamine hydrochloride. The filtrate is concentrated to a solid residue which is dried in vacuo at 80° C. for 25 hours. The dried sample is found to have the following composition: C, 62.55%, H, 7.68%, P, 10.78%; N, 0.25%; Cl, 0.19%.

EXAMPLE 5

The procedure of Example 4 is repeated using 21.2 g. (0.05 mol) of bis-(2-hydroxy-3,5-ditertiarybutylphenyl) methane as the bis-(hindered phenolic) reactant. Elemental analysis of the solid product shows the following composition: C, 65.98%; H, 8.62%; P, 9.85%, N, 0.17%; Cl, 0.04%.

EXAMPLE 6

The procedure of Example 5 is repeated using 19.4 g. (0.05 mol) of 4,4'-butylidene-bis-(5-tertiarybutyl-m-cresol) as the bis-(hindered phenolic) reactant. Elemental analysis of the solid product shows the following: C, 64.58%, H, 8.13%; P, 10.12%; N, 0.30%; Cl, 0.55%.

EXAMPLE 7

The procedure of Example 4 is repeated using 17.0 g. (0.05 mol) of 4,4'-butylidene-bis-(2-tertiarybutylphenol) as the bis-(hindered phenolic) reactant. Elemental analysis of the solid product shows the following composition: C, 63.47%; H, 7.79%; P, 10.42%; N, 0.27%; Cl, 0.14%.

It will be seen that the products prepared according to the procedures of Examples 4 and 5 are not illustrative of the invention because, in the one case, both positions ortho to the phenolic group are occupied by alkyl substituents, and in the other case, the phenolic group is not in the para position with respect to the bridging group, e.g., the methylene group.

The aromatic polyphosphites of this invention are useful as polymer additives. They provide thermal stability to polymer compositions, especially to olefin polymer compositions. For such use, preferred concentrations are from about 0.01 to about 1.0 percent, based on the weight of polymer. Ordinarily, the aromatic polyphosphites are used in such concentrations in combination with polyvalent metal oxides or salts of fatty acids in the stabilization of polypropylene; the polyvalent metal oxide or salt preferably is an alkaline earth metal stearate and is used in concentrations of from about 0.05 to about 1.0 percent based on the weight of polypropylene.

Those aromatic polyphosphites herein having at least two pentaerythritol residues and three bis-(hindered phenolic) residues are especially effective polymer additives because of their unusual thermal stability. Their effectiveness is shown by the data in Table I wherein the test samples are subjected to thermal gravimetric analysis. In this test a carefully weighed sample is heated at gradually increasing temperatures while the loss in weight of the sample is noted. The temperature required to produce a given percent weight loss, e.g., 10%, 20% and 50%, is taken as a measure of the relative thermal stability of the sample. Thus, if a sample has suffered a 50% weight loss by the time the temperature has reached 350° C., it i regarded as more stable, for example, than a sample which has loss that much weight at 300° C.

In the tests here, the samples are heated under ordinary atmospheric conditions.

TABLE I

| % Weight Loss | DPD* | Product of Ex. 2 | Product of Ex. 1 |
|---|---|---|---|
| onset | 110–120° C. | 130° C. | 190° C. |
| 10% | 222° C. | 250° C. | 295° C. |
| 20% | 270° C. | 285° C. | 340° C. |

TABLE I-continued

| % Weight Loss | DPD* | Product of Ex. 2 | Product of Ex. 1 |
|---|---|---|---|
| 50% | 311° C. | 360° C. | 400° C. |

*DPD: distearyl pentaerythritol diphosphite

The data above shows the clearly superior thermal stability of the higher molecular weight aromatic polyphosphite, i.e., the product of Example 1, which has at least two pentaerythritol residues and three bis-(hindered phenolic) residues.

Another method of testing the stabilizing influence of a test sample involves subjecting a polymer composition to repeated extrusions and determining the melt index after each such extrusion. A rapid increase in the melt index with repeated extrusions indicates a deterioration of the polymer.

The data of Table II is taken after 1, 3 and 5 extrusions of four test samples. Each sample contains 100 parts of polypropylene, 0.05 phr (parts per hundred parts of resin) of calcium stearate, 0.08 phr of Irganox 1010* and 0.07 phr, if any, of stabilizer.

*pentaerythritol tetrakis-3-(3,5-ditertiarybutyl-4-hydroxy-phenylpropionate).

TABLE II

| Stabilizer | Melt Index After Extrusion No. | | | |
|---|---|---|---|---|
| | 1 | 3 | 5 | AMI** |
| 1. None | 8.7 | 23.3 | 42.9 | 40 |
| 2. BHT (butylated hydroxytoluene) | 4.5 | 7.1 | 13.4 | 10.5 |
| 3. Tris(nonylphenyl) phosphite | 3.5 | 5.0 | 8.9 | 6.0 |
| 4. Product of Example 1 | 3.3 | 4.8 | 5.9 | 3.0 |

**AMI: Melt Index after 5th Extrusion minus 2.9 (Melt Index before 1st Extrusion).

Hydrolytic stability is an important property in polymer stabilization, especially where phosphites are concerned. This is so because many phosphite esters are quite unstable in the presence of atmospheric moisture. Frequently, it is necessary to add a small proportion of an amine to the phosphite to impart increased hydrolytic stability to it, or to encapsulate the phosphite with a wax which will melt during polymer processing to liberate the phosphite. A more desirable solution to this problem of hydrolytic instability, however, is to find a phosphite which is both an effective polymer stabilizer and is also hydrolytically stable.

The polyphosphites herein meet those two criteria: they are effective polymer stabilizers (as shown in Tables I and II), and they are relatively stable in the presence of atmospheric moisture. This latter property is shown by the data in Table III. Samples of the products prepared as in Examples 4–7 are stored in a controlled environment where the relative humidity is 74% (room temperature). The weight gain (corresponding to moisture absorption) is noted at the conclusion of 1, 3, 7 and 10 days. It will be seen that the polyphosphites of the invention (Examples 6 and 7) are superior, with respect to hydrolytic stability, to those outside the scope of the defined invention (Examples 4 and 5).

TABLE III

| | % Weight Gain After Day | | | |
|---|---|---|---|---|
| | 1 | 3 | 7 | 10 |
| Example 4 | 0.63 | 1.58 | 7.25 | 13.25 |
| Example 5 | 0.12 | 1.19 | 10.71 | 17.06 |
| Example 6 | — | 0.11 | 0.36 | 1.91 |

TABLE III-continued

| | % Weight Gain After Day | | | |
|---|---|---|---|---|
| | 1 | 3 | 7 | 10 |
| Example 7 | 0.28 | — | 0.21 | 0.30 |

The effectiveness of the polyphosphites herein as stabilizers alone, i.e., in the absence of such co-stabilizers as Irganox 1010 (see Table II), is shown by the data in Table IV. There, the samples shown each contain 100 parts of polypropylene plus 0.10 phr of the indicated additive. The melt index after various extrusions is obtained as in Table II.

TABLE IV

| | Melt Index After Extrusion No. | | | | |
|---|---|---|---|---|---|
| Stabilizer | 1 | 2 | 3 | 4 | 5 |
| 1. Distearyl Pentaerythritol Diphosphite | 10.3 | 30 | (too fast to measure) | | |
| 2. BHT | 6.2 | 8.1 | 9.2 | 13.8 | 14.5 |
| 3. Product of Example 2 | 5.8 | 6.3 | 7.2 | 8.3 | 10.3 |

Other polymers also are stabilized by the polyphosphites of this invention. A polycarbonate composition, for example, containing 100 parts of an aromatic polycarbonate (prepared by reaction of a dihydric phenol such as bisphenol-A with a carbonate precursor such as phosgene ... the disclosure of such aromatic polycarbonates in U.S. Pat. No. 4,066,611 is incorporated herein by reference), 0.05 phr of microthene wax ans 0.03 phr of the product of Example 6 is homogenized on a two-roll mill at 455°–475° C. for five minutes, then aged in an air-circulating oven at 140° C. for 24 hours. Initial color (after milling) and final color are noted for such sample and similar samples containing no phosphite ester and two other well-known phosphite polymer stabilizers. Less color in each case is noted for the sample containing the polyphosphite of this invention.

All parts and percentages herein are by weight unless otherwise expressly stated.

I claim:

1. An oligomeric, phenol-free, polyphosphite conforming to the structural formula:

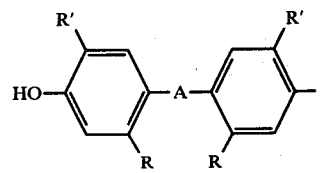

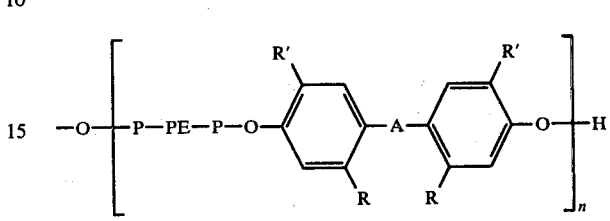

where R is methyl or hydrogen R' is a tertiary alkyl, cycloalkyl or phenylalkyl group of 4–10 carbon atoms, A is alkylidene or sulfur, PE is a pentaerythritol residue and n is at least 2.

2. The oligomeric, phenol-free polyphosphite of claim 1 wherein n is 2–10.

3. The oligomeric, phenol-free polyphosphite of claim 1 where R' is tertiarybutyl.

4. A polymer composition comprising a major proportion of a polymer normally subject to deterioration at elevated temperatures and a minor proportion effective to inhibit such deterioration of the composition of claim 1.

5. The polymer composition of claim 4 wherein n is 2–10.

6. The polymer composition of claim 4 wherein R' is tertiarybutyl.

7. The polymer composition of claim 4 wherein R is methyl.

8. The polymer composition of claim 4 wherein the polymer is a polyolefin.

9. The polymer composition of claim 4 wherein the polymer is polypropylene.

10. The polymer composition of claim 4 wherein the polymer is a polycarbonate.

* * * * *